United States Patent [19]

Krauser

[11] Patent Number: 5,316,476
[45] Date of Patent: May 31, 1994

[54] DENTAL IMPLANT WITH A LONGITUDINALLY GROOVED CYLINDRICAL SURFACE

[76] Inventor: Jack T. Krauser, 3017 Embassy Dr., West Palm Beach, Fla. 33409

[21] Appl. No.: 901,510

[22] Filed: Jun. 19, 1992

[51] Int. Cl.⁵ .............................................. A61C 8/00
[52] U.S. Cl. ................................................... 433/173
[58] Field of Search ........................ 433/173, 174, 175

[56] References Cited

U.S. PATENT DOCUMENTS

| | | | |
|---|---|---|---|
| 4,668,191 | 5/1987 | Plischka | 433/174 |
| 4,790,753 | 12/1988 | Frandera | 433/174 |
| 4,793,808 | 12/1988 | Kirsch | 433/173 |
| 4,824,372 | 4/1989 | Jörnéus | 433/174 |
| 4,856,994 | 8/1989 | Lazzara et al. | 433/174 |
| 4,904,187 | 2/1990 | Zingheim | 433/173 |
| 4,932,868 | 6/1990 | Linkow et al. | 433/174 |
| 4,934,935 | 6/1990 | Edwards | 433/174 |
| 4,960,381 | 10/1990 | Niznick | 433/174 |
| 5,026,280 | 6/1991 | Dürr et al. | 433/175 |
| 5,026,285 | 6/1991 | Dürr et al. | 433/173 |
| 5,049,073 | 9/1991 | Lauks | 433/174 |
| 5,073,111 | 12/1991 | Daftary | 433/174 |
| 5,100,323 | 3/1992 | Friedman et al. | 433/173 |

FOREIGN PATENT DOCUMENTS

| | | | |
|---|---|---|---|
| 0445667 | 9/1991 | European Pat. Off. | 433/173 |
| 2636832 | 3/1990 | France | 433/174 |

OTHER PUBLICATIONS

Michael S. Block, DMD; Israel M. Finger, BDS; Mark G. Fontenot, DDS, Meng; John N. Kent, DDS-"Loaded Hydroxylapatite-Coated and Grit-Blasted Titanium Implants in Dogs", *The International Journal of Oral and Maxillofacial Implants*, vol. 4, No. 3, 1989, pp. 219-295.

*Primary Examiner*—John J. Wilson
*Attorney, Agent, or Firm*—Harry W. Barron

[57] ABSTRACT

A dental implant for holding a dental prosthesis in place, after implantation within a hole drilled in bone, includes an upper surface, a generally cylindrical portion with a plurality of longitudinal shallow grooves, and an apical portion. The shallow circumferential grooves permit bone to grow entirely therein, so that the entire exposed surface of the implant has bone adhered thereto. The apical portion has a continuous truncoconical surface for diffusing the stresses into the bone. The head and uppermost portion of the cylinder have a smooth metal surface to retard the attachment of bone after implantation, while the remaining portion of the implant has either a roughened metal surface or a bioactive coating, such as hydroxylapatite, fluorapatite, or a bioactive carbon for the purpose of promoting the attachment of bone. A cap, having an outward expanding truncoconical head, is attached to the implant before implantation and left in place during a healing process to keep the upper portion of the implant free of tissues and ready for the attachment of a prosthesis.

23 Claims, 2 Drawing Sheets

DENTAL IMPLANT WITH A LONGITUDINALLY GROOVED CYLINDRICAL SURFACE

BACKGROUND OF THE INVENTION

Field of the Invention

This invention relates to a dental implants used to form root analogues for the attachment of dental prostheses, and more particularly, to such a dental implant having no externally threaded surfaces, particularly configured for use in areas of relatively low bone density.

Background Information

Cylindrical dental implants have been in use since 1976, with several different designs being incorporated into dental therapy. A dental implant is used where there are missing teeth, to act as a root analogue supporting a dental prosthetic device fitting on top of the implant. Such an implant typically has an internal threaded hole, extending inward from a hexagonally shaped surface portion, to be used for the attachment of a dental prosthetic device. The prosthesis is then screwed onto the implant, with an intermediate portion of the prosthesis engaging the hexagonal portion of the implant to prevent rotation. The implant includes a generally cylindrical portion extending from the surface portion to an apical portion at the opposite end.

Some dental implants have helically threaded exterior cylindrical surfaces and are normally inserted in dense bone areas such as the front jaw. These implants are literally screwed into properly sized holes drilled into the bone. Other dental implants are generally cylindrical shaped, without threads, and are placed into holes previously drilled into the bone. These non-threaded implants have surface designs adapted for the attachment to new bone growth. Conventional non-threaded cylindrical implants have openings extending through their apical portions for the intended purpose of permitting a space to accommodate new bone growth. However, recent research has shown that new bone growth does not predictably fill these openings. For example, the article by M. S. Block, I. M. Finger, M. G. Fontenot, and J. N. Kent, entitled "Loaded Hydroxylapatite and Grit-Blasted Titanium Implants in Dogs", in The International Journal of Oral & Maxillofacial Implants, Volume 4, pages 219 through 25, clearly shows that new bone does not completely fill these openings.

Chemical coatings and textured surfaces are also used to promote the attachment of bone to the implant. The Block et al article evaluated the response of canine mandibular bone to loaded hydroxylapatite coated and grit blasted titanium dental implants, and concluded that while soft tissue pocket depths were not statistically different, and crestal bone loss was not significantly different, the hydroxylapatite coated implants had a statistically significant greater amount of bone contacting their axial and apical surfaces. The implants used in this study included cylindrical axial portions with apical portions having cross drilled radial holes extending therethrough, and hemispherical apical ends.

One important function of the dental implant is the transmission of forces, generated by chewing actions on the prosthesis, into forces applied to the bone surrounding the implant, at stress levels compatible with the growth and maintenance of health bone tissue. Such stresses stimulate the surrounding bone, and, in accordance to Wolff's Law, if bone is not stimulated it will atrophy, whereas, if bone is over stimulated it will resorb in a process in which the calcified matrix dissolves away, lowering the density of the bone.

DESCRIPTION OF THE PRIOR ART

U.S. Pat. No. 4,668,191, issued to Plischka on May 26, 1987, describes a jaw implant, preferably made of aluminum oxide, having a screw head portion, and a lower cylindrical portion with an external helical screw thread extending to a spherically rounded end. The screw head portion has a flat outer surface, from which a central square hole descends into the head to accommodate the shank of a replacement tooth holder. The portion of the screw head provided for embedment into cortical bone tissue is not smaller than the outer diameter of the helical thread, while the screw head portion provided to extend through the gingivae increases in diameter while descending from the outer surface, through a truncoconical portion, before reducing to the diameter of the portion provided for embedment into bone.

U.S. Pat. No. 4,790,753, issued to Frandera on Dec. 13, 1988, describes a jaw implant, preferably made of titanium, consisting of a hexagonal screw head portion, a cylindrical lower portion with a helical exterior screw thread, and an intermediate frustoconical portion providing a ledge surface at the lower edge of the hexagonal portion, tapering down in diameter to the helically threaded lower portion. The apical portion of the implant includes a tapered portion extending to the end from the screw thread, while a central hole and a transverse slot extend upward from the end. This hole, the slot, and their intersection provide sharp edges in the apical region.

In the Frandera implant, an internally threaded hole extends downward from the upper surface of the hexagonal portion, and a cap with a central hole is provided to be fastened over the hexagonal portion, by means of a screw engaging the internally threaded hole. Attached in this way, the cap extends downward to align with the ledge surface, preventing the growth of gingival tissue over this ledge and around the hexagonal portion during the waiting period between implantation and fitting the dental prosthesis. This waiting period is required to allow healing and strengthening of the connection between the implant and surrounding bone tissue before the forces generated using the prosthesis are applied to the implant.

U.S. Pat. No. 4,793,808, issued to Kirsch on Dec. 27, 1988, describes means for attaching a dental prosthesis to a cylindrical implant. An implant post, which may be made using a synthetic elastically deformable material, is screwed into a threaded hole in the top surface of the implant. A fastening head, with a conical portion extending upward into the prosthesis, forms an upper portion of the implant post. A threaded hole extends downward from the top of the conical portion for the attachment, with a screw, of a prosthesis, which is thereby aligned to and pressed over the conical portion. Alternately, angular adjustment of the prosthesis may be provided by screwing a ball into place over the conical portion, with the prosthesis being attached to a socket engaging the surface of the ball and being locked thereto by an additional screw. The implant shown by Kirsch has a cylindrical body extending downward to a hemispherical apex. A pair of openings having cylindrically rounded edges extends entirely through the lower portion of the cylinder. The implant consists preferably of titanium, being highly polished on its upper end, while the lower part is roughened by knurling or sand blasting, or is coated with a titanium plasma process or with hydroxylapatite.

U.S Pat. No. 4,824,372, issued to Jörnéus et al on Apr. 25, 1989, describes a substantially tubular spacer used for the attachment of a single tooth restoration to a cylindrical implant. A screw, with a head pressing on an annular shoulder of the tubular spacer and a threaded portion engaging a threaded central hole of the implant, is used to fasten the tubular spacer to the implant. A tool provided for this fastening operation has a central part engaging a slot in the screw and an outer part engaging the tubular spacer, so that equal but counter-directed torques can be applied to the screw and spacer, thereby eliminating torsional loading of the implant during the installation of the spacer. The implant shown by Jörnéus et al is of the type having an external thread adapted to be screwed into bone. In the apical region, the Jörnéus et al implant includes a tapered section used to align the implant with the hole drilled in the surrounding bone to receive it, sharp edged flutes so that threads can be cut into the bone as the implant is screwed inward, a cylindrical cavity extending upward from a flat lower surface, and a number of apertures extending radially through to this cavity from the outer surface.

U.S. Pat. No. 4,932,868, issued to Linkow, et al on Jun. 12, 1990, describes an implant having an external threads with flutes extending between a head and an unthreaded apical portion. The apical portion also includes a tapered portion and a flat bottom from which a cylindrical cavity extends upward. Slots are cut through the lower part of the threaded portion and the upper part of the unthreaded apical portion, extending into the cylindrical cavity. Edges of these slots form surfaces for cutting threads into the surrounding bone, and the slots carry bone chips downward and inward, so that they are directed at the base of the hole bored in the bone.

U.S. Pat. No. 4,934,935, issued to Edwards on Jun. 19, 1990 describes the use of an anchor, or cylindrical implant, together with an intermediate transmucosal spacer member for mounting a dental prosthesis with a post. The transmucosal spacer and the post constitute, in effect, an axially offset extension of the implant, the angle of offset of the post axis being variable and selectable by relative rotation of parts at a bonded and preferably keyed plug and socket connection between the spacer member and one end of the implant. Several implants are shown, each of which has a cylindrical shank portion above a helically threaded portion. The apical end of the implant is a shallow dome having sharp edges below a annular groove, and parallel flats, to interlock with bone. The apical ends and threaded portions of the implants further have one or more holes extending therethrough.

U.S. Pat. No. 4,960,381, issued to Niznick on Oct. 2, 1990 describes an implant having an external helical thread and an internal threaded hole, with an internal structure at an end of the internal hole for engaging a rotationally driving insertion tool. The distal, or apical, end has a cylindrical hole extending upward to intersect with a radial hole extending through the part.

U.S. Pat. No. 5,026,280, issued to Dürr et al on Jun. 25, 1991, describes a method for mounting a conditionally removable denture, or prosthesis, on a threaded post extending through a centering collar to be fastened into a screw assembly in turn fastened into a cylindrical implant. The implant shown is of a type not having external helical threads, with a hemispherical apical end and a pair of vertically oriented parallel slots extending through the lower part of the cylindrical portion. The ends of the slots are cylindrically rounded.

U.S. Pat. No. 5,026,285, issued to Dürr et al on Jun. 25, 1991, describes the use of a spacing element having two external threaded surfaces, the first of which engages the internal threads of a cylindrical dental implant, and the second of which engages a ring element fastened on top of the implant. A tool for fastening these elements in place includes concentric sleeves, one of which engages a head of the spacing element, while the other engages the ring element.

U.S. Pat. No. 5,100,323, issued to Friedman et al on Mar. 31, 1992, describes a dental implant having an unthreaded cylindrical body with a hexagonal head portion extending outward form an annular base. A generally cylindrical abutment with a face having a female hexagonal surface, configured to engage the head portion of the implant, is provided for use in the attachment of a prosthetic device by means of a screw extending through an unthreaded hole in the abutment to engage a threaded hole in the implant. The engagement of the hexagonal surfaces is used to prevent rotation of the abutment relative to the implant. The apical portion of the implant is similar to that described in U.S. Pat. No. 5,026,280 to Dürr.

The types of implants of the prior art having external screw threads, adapted to be screwed into place and to form an internally threaded surface in the bone as they are so installed, have been shown to be relatively unsuitable for use, particularly in areas of lower bone density. Examples of implants having such threads are found in U.S. Pat. Nos. 4,668,191 to Plischka, 4,790,753 to Fradera, 4,932,868 to Linkow et al, 4,934,935 to Edwards, and 4,960,381 to Niznick. The unthreaded implants of the prior art have all included openings through the wall which creates problems when the bone attempts to grow thought the opening. Further, the bottom of the implant devices have not been designed to distribute the forces on the implant, such as from chewing, evenly into the bone in a manner best able to prevent atrophy or resorption of the bone. A dental implant device overcoming these problems is needed.

SUMMARY OF THE INVENTION

In accordance with one aspect of the invention, there is provided an integral dental implant including an upper end having an upper surface and an apical end, having a lower surface, opposite to the upper surface. The apical end further has a truncoconical surface extending from the lower surface toward the upper surface, the truncoconical surface being continuous and increasing in diameter along an axis from the lower surface to the upper surface. The implant further includes an generally cylindrical portion extending between the upper end and the apical end, which includes a plurality of longitudinally extending grooves in the surface thereof. Finally, the implant includes attachment means extending axially inward from the upper surface.

BRIEF DESCRIPTION OF THE DRAWINGS

Preferred embodiments or variations of the subject invention are hereafter described, with specific reference being made to the following Figures, in which.

DETAILED DESCRIPTION

Figure 1:
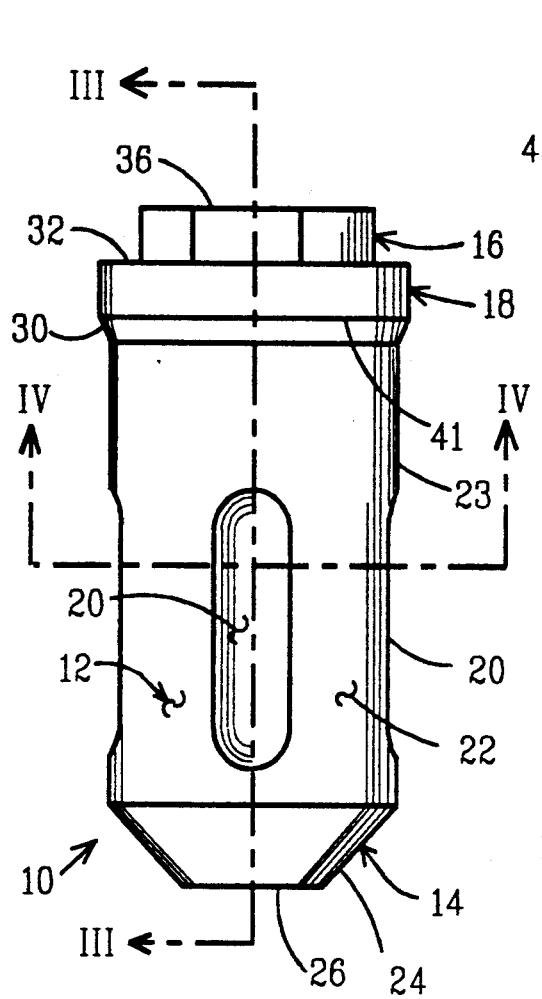
FIG. 1 is a side elevation of a cylindrical dental implant made in accordance with the present invention.
Figure 3:
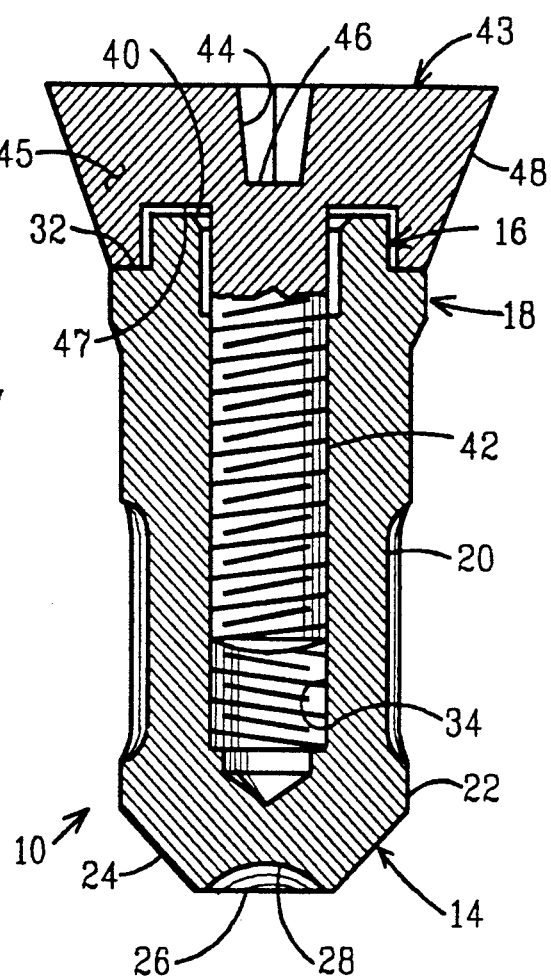
FIG. 3 is a longitudinal cross-sectional view of the implant of FIG. 1, taken as indicated by section lines III—III in FIG. 1, showing in addition an attached cover screw.
Figure 2:
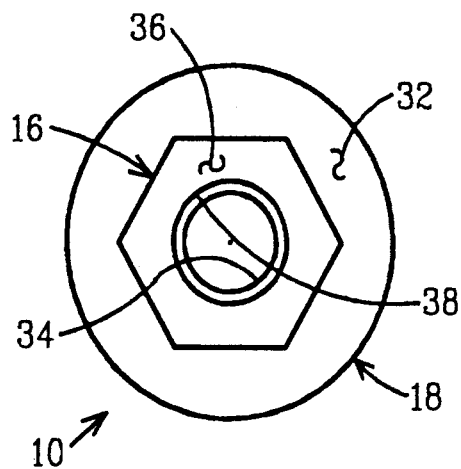
FIG. 2 is a top elevation of the implant of FIG. 1.
Figure 4:
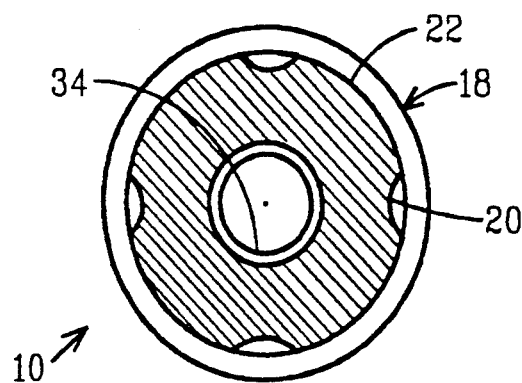
FIG. 4 is a transverse cross-sectional view of the implant of FIG. 1, being taken as indicated by section lines IV—IV in FIG. 1.

FIGS. 1 through 4 show a first version of a dental implant made in accordance with the present invention, with FIGS. 1 and 2 being, respectively, side and top elevational views thereof, while FIGS. 3 and 4 are cross-sectional views taken asindicated, respectively, by lines III—III and IV—IV of FIG. 1.

Referring first to FIG. 1, a dental implant 10, which is preferably made from titanium or a titanium alloy, includes a generally cylindrical portion 12, an apical portion 14, a hexagonal head 16 (the shape of which is more clearly shown in FIG. 2), and a flange 18 between generally cylindrical portion 12 and head 16. Cylindrical portion 12 includes a number of longitudinally extending grooves 20, which provide gentle transitions in the shape of the surface. The shape of each groove 20 is shown particularly in the cross-sectional views of FIGS. 3 and 4. Generally, each groove 20 is shaped as an arcuate cylinder section extending into the surface 22 of cylindrical portion 12 and orientated parallel to the axis of cylindrical portion 12. The ends of each groove 20 are spherically rounded to provide a gentle transition in surface shape in both the longitudinal direction and the circumferential direction. Grooves 20 extend only slightly, if at all, into the upper half 23 of cylindrical portion 12, where a smooth cylindrical surface is provided without interruption.

As shown in FIG. 3, apical portion 14 includes a truncoconical surface 24 extending between cylindrical surface 22 and a flat annular bottom surface 26. A spherically rounded dimple 28 extends centrally into bottom surface 26. Flange 18 extends diametrically outward above cylindrical surface 22 and is connected to cylindrical surface 22 by a transition region 30. Flange 18 has a flat annular ledge 32 around hexagonally shaped head 16. Dental implant 10 also includes an internally threaded attachment hole 34 extending centrally inward from an upper surface 36 of head 16. The upper parts of attachment hole 34 include a cylindrical counterbore hole 38 and a small countersink 40.

In preferred usage, dental implant 10 is used to provide a root analogue to support an attached dental prosthetic device (not shown) in the rearward portion of the mouth, where bone is less dense than in the front of the jaw. The dental prosthetic device may be, for example, a single replacement tooth or a structure having two or more replacement teeth. In preparation for the insertion of implant 10, a hole is drilled in the bone by conventional techniques. Then implant 10 is inserted into the hole, with apical portion 14 being directed inward, and the insert is pushed into place. As noted above, grooves 20 do not extend into the upper portion of cylindrical portion 22. The reason for this structure is to provide a tight fit can between the upper surface of the implant and the hole drilled in the bone. A tight fit in this region blocks a potential pathway through which bacteria and other agents of infection might otherwise gain access to the hole drilled in the bone before the healing process is completed. An ungrooved length of 3 to 4 millimeters in the upper portion of cylindrical portion 12 is adequate for this purpose.

While the language used herein, along with the orientation of the Figures, may imply that hexagonal head 16 is an upwardly directed feature, it is to be understood that implant 10 can be used in both mandibular and maxillary applications, with the hexagonal head 16 always being directed outwardly from a hole drilled in the bone and apical portion 14 always facing the bottom of the hole.

After a suitable healing period, which provides time for new bone tissue to grow along various surfaces of implant 10, a dental prosthesis is attached to the top surface 36 of hexagonally shaped head 16 by means of a screw engaging attachment hole 34. The hexagonal shape of head 16 is provided to prevent rotation of the prosthesis relative to implant 10. The prosthesis, or an attachment device between the prosthesis and implant 10, has a cavity which engages head 16 when it is held downward by a screw engaging attachment hole 34. For example, the prosthesis or attachment device may include a hexagonal cavity fitting over head 16, extending to ledge 32 of flange 18.

The establishment and maintenance of healthy bone tissue in attachment with, or at least in very close proximity to, various surfaces of implant 10 is key to the success of any implant operation. To promote proper bone development, all surfaces below lower edge 41 of flange 18, including transition surface 30, cylindrical portion 12, and apical portion 14, are coated with a bioactive coating which attracts the growth of body tissue. For example, in a preferred embodiment, hydroxylapatite may be used. Alternatively, fluorapatite, bioactive carbons, and other bioactive materials may be used to coat the surfaces below edge 41. Instead of a bioactive coating, a controlled roughening of the metal surface may be used to promote adjacent bone attachment. According to the Block et al article, a titanium alloy (Ti-6Al-4V) can be grit blasted with 24 grit alumina particles at a pressure of 80 pounds per square inch for 10 seconds to create 25 to 50 micron irregularities, forming a surface suitable for this purpose. An alternate method for producing a suitable surface roughness on a titanium part is the flame spraying of titanium from a plasma.

Since it has been shown through animal studies that bone resorbs away from highly polished metal, hexagonal head 16 and flange 18 above lower edge 41 have highly polished surfaces without the surface roughening or coating described above. These upper surfaces of implant 10 are thus reserved for the adjacent growth of gingival tissue and for mating structures extending from the dental prosthesis or an attachment device between the prosthesis and implant 10. While U.S. Pat. No. 4,793,808 to Kirsch teaches the use of a titanium implant which is highly polished on its upper end, with a roughened or coated lower end, the advantage of the present invention is that the level of bone attachment is specifically limited by extending the polished metal of implant 10 down its side. A suitable demarcation between bone and gingival tissue is provided if the height, in the axial direction, of flange 18 is between 0.5 and 1.0 millimeter. Head 16 preferably extends between 0.7 millimeter and 1.5 millimeters above ledge 32, with 0.7 millimeter being the conventional distance, while 1.5 millimeters provides better retention of a single tooth prosthesis.

Since studies have shown that bone does not fully grow through radial cavities extending entirely through dental implants, cavities entirely through the implant are not included in implant 10. In the prior art implants, the material of the implant forms a stress shielded central section, to which the stresses produced by mastication and other forces acting on the implant are not transmitted at a level sufficient for the growth and maintenance of healthy bone tissue in accordance with Wolff's Law. To overcome these problems of the prior art, cylindrical surface 22 of implant 10 remains generally continuous, except for the depressed regions formed by shallow grooves 20, and truncoconical surface 24 remains continuous. The general design of implant 10 remains one of relatively gentle changes in surface shapes, without deep slotted grooves, holes, and right angle edges.

Truncoconical surface 24 is of a shape which can be easily produced by machining or forging apical end 14 of implant 10. Also, the truncoconical shape mates with the end of a hole which can be easily drilled into bone with a properly shaped drill, and so that a close fit can be easily obtained. More importantly, truncoconical surface 24 transforms vertical forces on implant 10, caused by mastication, into outwardly radiated stresses in the adjacent bone tissue, thereby maintaining even stress levels compatible with the growth and maintenance of healthy bone tissue. While a full conical shape could be used to accomplish the same force transformation, it is less desirable than the truncoconical shape because of the additional depth required for a complete conical shape.

Apical end dimple 28 allows hemodynamic back pressure to be used to provide a venting area during the seating of implant 10 in a cavity drilled in bone. Thus, apical end of implant 10 demonstrates advantages over the prior art hemispheric end for an implant without external threads shown, for example, in U.S. Pat. Nos. 4,793,808 to Kirsch and 5,026,280 to Dürr et al and 5,100,323 to Friedman. In other prior art examples of implants having external threads, a truncoconical apical surface is used for alignment with a hole drilled in the bone, while vertical forces are transmitted between the implant and surrounding bone through the threads of the implant, rather than the bottom of the implant.

After the implantation of implant 10, bone tissue easily grows entirely into the spaces provided by shallow grooves 20 along generally cylindrical portion 12. Bone occupying the space within groove 20 is particularly useful in resisting any torque which might be applied about the axis of implant 10. However if significant stress is applied to the bone, it may fracture. In implant 10, the large angle between the interior surface of groove 20 and surface 22 of cylindrical portion 12, (which is significantly closer to 180 degrees than ninety degrees), results in no sharp angular stress points in the new bone growth. To further eliminate the bone stress, the edge between groove 20 and surface 22 may be rounded. Furthermore, the apical ends of grooves 20, when grooves 20 are filled with bone tissue, prevent outward motion of implant 10, which might occur, for example, if the dental prosthesis attached to implant 10 became adhered to a sticky food substance. Thus, the surfaces of cylindrical portion 12 and apical portion 14, without a radial opening extending therethrough, have maximized surfaces for the development of adjacent bone tissue, and optimized geometries for the transfer of forces to adjacent bone tissue.

Referring again to FIG. 3, in accordance with a preferred version of the invention, implant 10 is supplied to the patient with a threaded portion 42 of cover screw 43 fastened in engagement with threaded hole 34. Cover screw 43 is fastened into implant 10 by means of a tool (not shown) engaging a non-circular aperture 44 in head 45 of screw 43. Aperture 44, which may be, for example, generally hexagonal in transverse shape, preferably has sides tapered inward so that inner surface 46 of aperture 44 is smaller than the opening of the aperture. In this way, the axial force provided when the tool (not shown) is pushed into aperture 44 is multiplied by a wedging action to produce a relatively high level of opposing radial forces, which facilitate handling screw 43 and implant 10 attached thereto by means of a tool (not shown) without screw 43 falling off the tool. Because of the difficulties in positioning an implant within the mouth of a patient, the facilitation of such handling is particularly important. Head 45 of cover screw 43 includes a recessed cylindrical area 47, which forms clearance spaces around head 16 of implant 10 so that screw head 44 is clamped against annular ledge 32 around implant head 16. Head 45 also includes a truncoconical outer surface 48, which is tapered to reduce in diameter in the direction in which threaded portion 42 extends.

In accordance with a preferred method of usage, implant 10 is installed in suitable hole drilled in the bone of a patient. During the installation, screw 43 remains firmly attached in hole 34. Screw 43 is left in place during the healing process, during which the growth of bone produces an implant structure strong enough to withstand the forces of mastication. After the healing process is complete, screw 43 is removed using a tool (not shown) imparting a rotational torque through aperture 44. After screw 43 is removed, a suitable dental prosthesis is installed using another screw (not shown) by conventional dental techniques. Using screw 43 in this way retains the surfaces of head 16 and ledge 32 free from tissue and ready for the subsequent attachment of a dental prosthesis.

While the outer surfaces of screw head 45 are smooth metallic surfaces which do not encourage the adjacent growth of bone tissues or of gingival tissues, in some applications such growth will occur, presenting a potential problem in the removal of screw 43. To minimize this problem, truncoconical outer surface 48 is provided, whereby the outward axial motion of screw 43 pulls surface 48 uniformly away from such tissues. The design of screw head 45, thus, has a significant advantage over conventional protection caps of the prior art which lack the truncoconical outer shape of a protecting cover. It is understood that the features described above with reference to screw 43 can be applied separately to a screw used with the traditional type of implant having a threaded hole for an attachment screw and cover used during the healing process following insertion of a dental implant.

Figure 5:
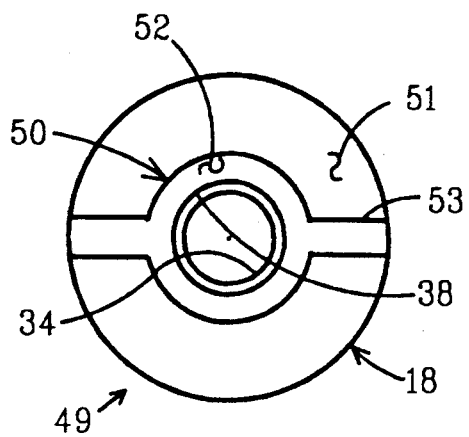
FIG. 5 is a top elevation of an implant having an alternate head structure.

FIG. 5 is a top view of a cylindrical dental implant 49 having a head 50, extending above an upper surface 51 of flange 18 to an upper surface 52, with a different shape than that of head 16 of implant 10. Since the purpose of head 16 or 50 is basically the prevention of rotation of the prosthesis, or attachment device, relative to the implant, various types of surfaces for providing one or more features for keying engagement, radially displaced from center of threaded attachment hole 34, may be used for the head 16 or 50 of an implant. Implant 49 has two such features in the form of outward extending raised keys 53. Thus, implant 49 is an alternative form, which may otherwise have features similar or identical to those of implant 10, built in accordance with the present invention.

Figure 6:
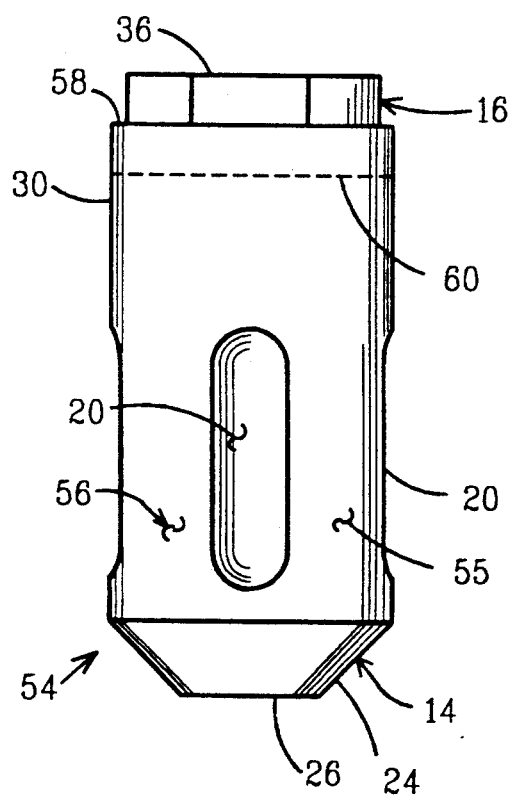
FIG. 6 is a side elevation of an alternative version of a cylindrical dental implant, without a flange between a head portion and a generally cylindrical portion, made in accordance with the present invention.

Referring now to FIG. 6, implant 54 is shown as another variation of the subject invention. In implants 10 and 49, flange 18 was provided to enlarge the area to which a dental prosthesis may be attached In some applications, this enlarged area is not required, so dental implant 54 is shown without an outward extending flange 18. In implant 54, a cylindrical surface 55 of a generally cylindrical portion 56 is extended to a ledge 58 below hexagonal head 16. Smooth, polished metal surfaces are provided above a level indicated by dashed line 60, while roughened metal surfaces or a bioactive surface coating, such as hydroxylapatite, are provided below line 60. To provide a suitable interface between bone and gingival tissue along the surface of implant 54, polished metal surfaces extend downward between 0.5 and 1.0 millimeter from ledge 58. Other aspects of implant 54, such as grooves 20 and apical portion 14, are as previously described portions of implant 10.

Figure 7:
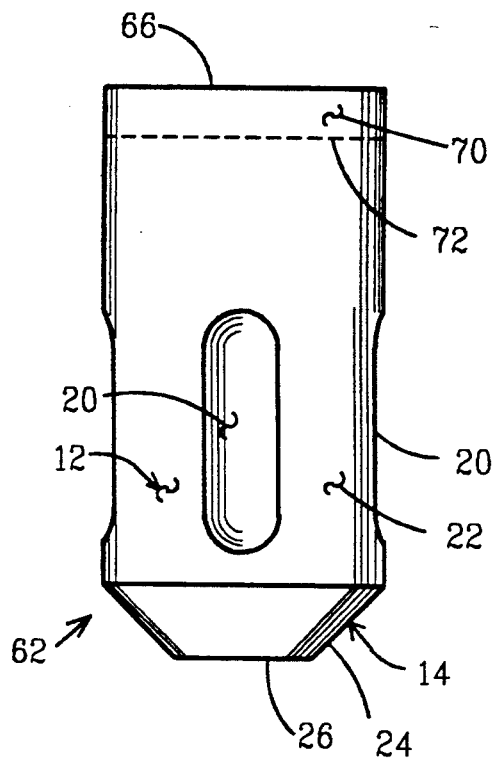
FIG. 7 is a side elevation of a second alternative version of a cylindrical dental implant, with a countersunk central hole instead of a head portion, also made in accordance with the present invention.

FIG. 7 shows an implant 62, which is another version of an implant built in accordance with the present invention. In implant 62, head 16 of implant 54 is eliminated, and, as shown in another alternative version of FIG. 8, a countersink 64 is provided to extend from an upper surface 66 into internally threaded hole 68. While the previously discussed implants 10, 49, and 54 include specific structure for preventing the rotation of a single tooth prosthesis attached to a single implant, implant 62 lacks that structure. Rather, implant 62 is designed for use where two or more implants are to be used for the attachment of a prosthesis including two or more replacement teeth. Countersink surface 64 can be used to center a prosthesis or attachment device fastened in place with a screw engaging threaded hole 68. Polished metal surfaces extend across the annular upper surface 66 of implant 62 and down cylindrical surface 70 for a distance preferably between 0.5 and 1.0 millimeter to a line 72, which indicates the beginning of a roughened or coated surface, as previously described with respect to implant 54 of FIG. 6.

Figure 8:
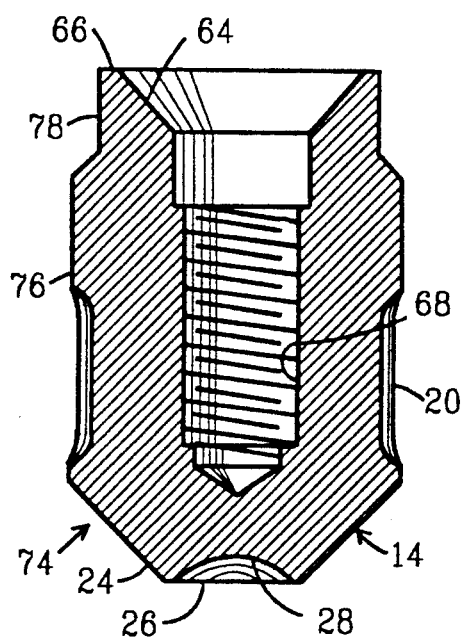
FIG. 8 is a longitudinal cross-sectional view of a third alternative version of a cylindrical dental implant, also made in accordance with the present invention, having a countersunk central hole and a generally cylindrical portion with an enlarged diameter.

FIG. 8 shows an implant 74, which is another version of an implant built in accordance with the present invention. Implant 74 has a generally cylindrical section 76 axially shortened and radially enlarged, to provide a suitable insert for use in the rear portions of the jawbone, where the bone is relatively wide, but where underlying nerves prevent drilling deeply. The countersunk attachment screw hole used in implant 62 is also used in implant 74. The diameter of the upper portion 78 of implant 74 is not increased with the increase in the diameter of section 76. Upper surface 66 has a smooth metallic surface, which extends down at least a portion of the side of upper portion 78 to retard the attachment or closely adjacent growth of bone tissue, while the remainder of the external surfaces of implant 74 are roughened or coated with a bioactive coating to promote such growth.

Screw 43, shown in FIG. 3, may also be applied to implants 62 and 74, with head portion 45 of screw 43 being sized to cover upper surface 66, keeping this surface 66 free from gingival and bone tissue during the healing process. In this application, recessed cylindrical area 47 is not required, although it does not interfere with the function of screw 43.

Along with the variations described above among types of implants made in accordance with the present invention, it is desirable to provide variations in the size of implants. Different sizes of implants are needed for different applications, as determined by factors such as the size of bones and dental features within the mount of a patient and by the specific location for which a prosthesis is needed. Implants 10, 49, 54, 62, and 74 can collectively be made in several diameters within a range typically between 2.9 millimeters and 6.0 millimeters. Within this range of diameters, suitable grooves 20 have a radius, as seen in a cross-sectional view such as FIG. 4, of 0.9 millimeter and are cut or formed to a depth of 0.3 millimeter below the surrounding cylindrical surface 22. Implants having diameters between, for example, 4.0 and 6.0 millimeters may have six equally spaced grooves 22, while implants having smaller diameters have four equally spaced grooves. The implants 10, 49, 53, and 62 can also be made in several lengths typically within a range between 4 millimeters and 20 millimeters.

The various types of implants described above can also be used to provide variations in the diameter of the generally cylindrical portion extending into the bone, as required to accommodate use in various types of bone structures, while the upper portion of the implant remains at a constant diameter to accommodate standard fittings for a prosthesis. For example, the diameter of the upper portion of the implant may remain at 4 millimeters, while the diameter of the lower portion varies between 2.9 millimeters and 6.0 millimeters, extending outward or inward from the upper portion.

It is to be understood that various other combinations of the features described herein are both useful and within the scope of this invention. For example, the outward-extending cylindrical portion of implant 74, shown in FIG. 8, can be usefully applied to an implant having a hexagonal head, like that of implant 10, shown in FIGS. 1 through 4.

What is claimed is:
1. An integral dental implant comprising:
   an upper end having an upper surface;
   an apical end, including a lower surface, opposite to said upper surface, and a trunconical surface extending from said lower surface toward said upper surface, said truncoconical surface being continu- ous and increasing in diameter along an axis from said lower surface to said upper surface;

a generally cylindrical portion extending between said upper end and said apical end including a plurality of longitudinally extending grooves in the surface thereof; and attachment means extending axially inward from said upper surface, wherein said upper end further includes a head extending downward from said lower surface to an outward extending ledge, said head having means for preventing axial rotation of a member affixed thereto;

wherein said generally cylindrical portion extends between said truncoconical surface and said outward extending ledge;

wherein said head, said outward extending ledge, and an upper portion of said generally cylindrical portion, adjacent to said outward extending ledge, have a smooth metallic surface; and wherein said apical end and the remaining portion of said generally cylindrical portion includes a bioactive coating.

2. The dental implant of claim 1, wherein said bioactive coating is a coating selected from a group consisting of hydroxylapatite, fluorapatite, and bioactive carbons.

3. The dental implant of claim 1 wherein said upper cylindrical portion includes a flange adjacent disposed between said head and said lower cylindrical portion and extending radially outward therefrom, said outward extending ledge forming an upper surface of said flange, said flange extending downward and inward from said ledge to said lower cylindrical portion.

4. The dental implant of claim 3 wherein said head, said outward extending ledge and said flange have smooth metallic surfaces and said lower cylindrical portion and said apical end have bioactive coating.

5. The dental implant of claim 4 wherein said bioactive coating is a coating selected from a group consisting of hydroxylapatite, fluorapatite, and bioactive carbons.

6. An integral dental implant comprising:
an upper end having an upper surface;
an apical end, including a lower surface, opposite to said upper surface, and a truncoconical surface extending from said lower surface toward said upper surface, said truncoconical surface being continuous and increasing in diameter along an axis from said lower surface to said upper surface;
a generally cylindrical portion extending between said upper end and said apical end including a plurality of longitudinally extending grooves in the surface thereof; and
attachment means extending axially inward from said upper surface,
wherein said upper end further includes a heat extending downward from said upper surface to an outward extending ledge, said head having means for preventing axial rotation of a member affixed thereto;
wherein said generally cylindrical portion extends between said truncoconical surface and said outward extending ledge;
wherein said head, said outward extending ledge, and an upper portion of said generally cylindrical portion, adjacent to said outward extending ledge, have a smooth metallic surface; and wherein said apical end and the remaining portion of said generally cylindrical portion have roughened surfaces.

7. The dental implant of claim 6 wherein said upper cylindrical portion includes a flange adjacently disposed between said head and said lower cylindrical portion and extending radially outward therefrom, said outward extending ledge forming an upper surface of said flange, said flange extending downward and inward from said ledge to said lower cylindrical portion.

8. The dental implant of claim 7 wherein said head, said outward extending ledge and said flange have smooth metallic surface and said lower cylindrical portion and said apical end have roughened surfaces.

9. An integral dental implant comprising:
an upper end having an upper surface;
an apical end, including a lower surface, opposite to said upper surface, and a truncoconical surface extending from said lower surface toward said upper surface, said truncoconical surface being continuous and increasing in diameter along an axis from said lower surface to said upper surface;
a generally cylindrical portion extending between said upper end and said apical end including a plurality of longitudinally extending grooves in the surface thereof; and
attachment means extending axially inward from said upper surface.
wherein said upper end further includes a head extending downward from said upper surface to an outward extending ledge, said head having means for preventing axial rotation of a member affixed thereto;
wherein said dental implant further includes an upper diameter than said head;
wherein said dental implant further includes an upper cylindrical portion and a transition portion, said upper cylindrical portion having a diameter of said outward extending ledge and extending longitudinally between said outward extending ledge and said transition portion; and said transition portion extending between said upper cylindrical portion and said generally cylindrical portion.

10. The dental implant of claim 9 wherein said head, said outward extending ledge, and an upper part of said upper cylindrical portion have smooth metallic surface and said generally cylindrical portion and said apical end have a bioactive coating.

11. The dental implant of claim 10 wherein said bioactive coating is a coating selected from a group consisting of hydroxylapatite, fluorapatite, and bioactive carbons.

12. The dental implant of claim 9 wherein said head, said outward extending ledge and an upper part of said upper cylindrical portion have smooth metallic surface and said generally cylindrical portion and said apical end have roughened surfaces.

13. A integral dental implant comprising:
an upper surface;
a first cylindrical surface extending downward from said upper surface;
a second cylindrical surface extending downward from said first cylindrical surface;
a plurality of circumferentially spaced grooves extending in a longitudinal direction around said second cylindrical surface, said grooves extending along the length of said second cylindrical surface;
an annular lower surface;

a continuous truncoconical surface extending between said lower surface and said second cylindrical surface;
a dimple extending within said lower surface; and
an attachment hole extending within said upper surface;
said second cylindrical surface, said grooves, said annular lower surface, and said dimple being processed to encourage bone adhesion thereto and said upper surface and first cylindrical surface being processed to retard bone adhesion thereto;
said first cylindrical surface extends 0.5 to 1.0 millimeters in an axial direction and is coextensive with said second cylindrical surface.

14. The dental implant of claim 13 further including a head extending axially outward from said upper surface, said head being processed to retard bone adhesion thereto.

15. The dental implant of claim 13 wherein said first cylindrical surface extends radially outward from said second cylindrical surface.

16. The dental implant of claim 13 wherein said second cylindrical surface extends radially inward from said first cylindrical surface.

17. The dental implant of claim 13 wherein said second cylindrical surface, said grooves, said annular lower surface, and said dimple are coated with a bioactive coating and said upper surface and first cylindrical surface are smooth metal.

18. The dental implant of claim 13 wherein said second cylindrical surface, said grooves, said annular lower surface, and said dimple are coated with a coating selected from a group consisting of hydroxylapatite, fluorapatite, and bioactive carbons, and said upper surface and first cylindrical surface are smooth metal.

19. The dental implant of claim 13 wherein said second cylindrical surface, said grooves, said annular lower surface, and said dimple are roughened metal and said upper surface and first cylindrical surface are smooth metal.

20. The dental implant of claim 13 wherein said grooves extend within said second cylindrical surface by an amount less than the distance between said second cylindrical surface and said attachment hole.

21. The dental implant of claim 20 wherein said grooves are generally cylindrical sections with spherical section ends.

22. The dental implant of claim 21 wherein the angle between said second cylindrical surface and said grooves is substantially greater than ninety degrees and less than 180 degrees.

23. The dental implant of claim 13 wherein said grooves extend downward from a longitudinal location at least three millimeters below an upper edge of said second cylindrical surface.

* * * * * ns
REEXAMINATION CERTIFICATE (2924th)
United States Patent [19]
Krauser

[11] B1 5,316,476
[45] Certificate Issued Jun. 18, 1996

[54] DENTAL IMPLANT WITH A LONGITUDINALLY GROOVED CYLINDRICAL SURFACE

[76] Inventor: Jack T. Krauser, 3017 Embassy Dr., West Palm Beach, Fla. 33409

Reexamination Request:
No. 90/003,701, Jan. 24, 1995

Reexamination Certificate for:
Patent No.: 5,316,476
Issued: May 31, 1994
Appl. No.: 901,510
Filed: Jun. 19, 1992

[51] Int. Cl.$^6$ ................................................. A61C 8/00
[52] U.S. Cl. ........................................................ 433/173
[58] Field of Search .............................. 433/173, 174, 433/175

[56] References Cited

U.S. PATENT DOCUMENTS

| | | | |
|---|---|---|---|
| 4,988,298 | 1/1991 | Lazzara et al. | 433/173 |
| 5,006,068 | 8/1991 | Lee et al. | 433/173 |
| 5,049,072 | 9/1991 | Lueschen | 433/173 |

OTHER PUBLICATIONS

Minimatic Implant Technology Inc. "Catalog of: Implants Prosthetic Components etc." May 1992.

Core-Vent Corp 1990 Product Catalog, Jul. 1990.

Obutment Osseointegrated Implant System, Aug. 1989.

Core-Vent Corp. "HA-Coated Screw Implants-The Inside Story".

Core Vent Corp. advertisement, Feb. 1991.

Bio-Vent literature.

Osseotite literature, "Osseotite: The Next Dimension in Implant Evolution".

L. A. Wolfe, PhD, et al. "Bone Response to a Matched Modulus Endosseous Implant Material", The International Journal of Oral & Maxillofacial Implants, 1989.

D. Siegele, "Numerical Investigations of the Influence of Implant Shape on Stress Distribution in the Jawbone", The International Journal of Oral & Maxillofacial Implants, 1989.

R. J. Lazzara, DMD; "Restorative Advantages of the Coronally Hexed Implant," Compend. Continuing Educ. Dent., vol. XII, No. 12.

M. S. Block, DMD, et al., "Use of the Integral Implant for Overdenture Stabilization," International Journal of Oral & Maxillofacial Implants, 1990.

R. D. Sager, DMD, et al., "Implant-retained Precision Two-stage Single-tooth Replacement" Journal of Oral Implantology, vol. XVII, No. 2, 1991.

"Dimples V. Holes in the Implant Body" Technical Monograph 9.

Boskovic, DDS, et al., "Solving the Problem of Violated Intermaxillary Space Caused by Poor Pre-planning and Improper Placement of Endosscous Implants: A Case Report", Journal of Oral Implantology, vol. XVIII, No. 1, 1992.

(List continued on next page.)

*Primary Examiner*—Nicholas D. Lucchesi

[57] ABSTRACT

A dental implant for holding a dental prosthesis in place, after implantation within a hole drilled in bone, includes an upper surface, a generally cylindrical portion with a plurality of longitudinal shallow grooves, and an apical portion. The shallow circumferential grooves permit bone to grow entirely therein, so that the entire exposed surface of the implant has bone adhered thereto. The apical portion has a continuous truncoconical surface for diffusing the stresses into the bone. The head and uppermost portion of the cylinder have a smooth metal surface to retard the attachment of bone after implantation, while the remaining portion of the implant has either a roughened metal surface or a bioactive coating, such as hydroxylapatite, fluorapatite, or a bioactive carbon for the purpose of promoting the attachment of bone. A cap, having an outward expanding truncoconical head, is attached to the implant before implantation and left in place during a healing process to keep the upper portion of the implant free of tissues and ready for the attachment of a prosthesis.

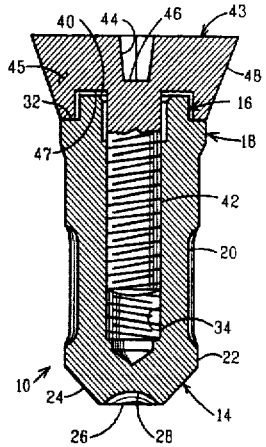

OTHER PUBLICATIONS

S. D. Cook et al., "The Effect of Surface Macrotexture on the Mechanical and Histologic Characteristics of Hydroxylapitite–coated Dental Implants", Journal of Oral Implantology, vol. XIX, No. 4, 1993.

"A Complete Line of Implants . . . " Steri–Oss Inc. Brochure, 1992.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-23 is confirmed.

* * * * *